(12) United States Patent
Lohrding et al.

(10) Patent No.: US 6,233,269 B1
(45) Date of Patent: May 15, 2001

(54) APPARATUS AND METHOD FOR PROTECTING COMPONENTS OF A LIGHT SOURCE

(75) Inventors: Ronald K. Lohrding; Michael A. Wolf; Jerome Conia; Richard D. Zigweid; David J. Costello; Barry A. Hudy, all of Albuquerque, NM (US)

(73) Assignee: Cell Robotics, Inc.

( * ) Notice: Subject to any disclaimer, the term of this patent is extended or adjusted under 35 U.S.C. 154(b) by 0 days.

(21) Appl. No.: 09/212,545

(22) Filed: Dec. 16, 1998

(51) Int. Cl.$^7$ ..................................................... H01S 3/00
(52) U.S. Cl. ................................................. 372/109; 606/2
(58) Field of Search ................................ 372/109; 606/9, 606/11, 16, 17

(56) References Cited

U.S. PATENT DOCUMENTS

| | | | |
|---|---|---|---|
| 3,578,839 | * | 5/1971 | Riggle ................................. 359/507 |
| 5,148,446 | | 9/1992 | Radich . |
| 5,554,153 | * | 9/1996 | Costello ................................... 606/9 |
| 5,908,416 | * | 6/1999 | Costello ................................... 606/9 |
| 5,993,439 | * | 11/1999 | Costello ................................... 606/9 |

* cited by examiner

*Primary Examiner*—Teresa M Arroyo
*Assistant Examiner*—Gioacchino Inzirillo
(74) *Attorney, Agent, or Firm*—Robert W. Becker & Associates

(57) ABSTRACT

An apparatus and method for protecting at least one component of a light source are provided. The apparatus includes a shield for the component, with this shield having a plurality of locations that are substantially transparent to an emission wave length of the light source. The shield is positioned such that during use of the light source, one of the substantially transparent locations of the shield is disposed between the at least one component of the light source and an object that is to be irradiated. The apparatus also includes a mechanism for advancing the shield upon activation of the light source or an element thereof in order to be able to dispose a different one of the substantially transparent locations of the shield between the at least one component of the light source and an object that is to be irradiated.

17 Claims, 4 Drawing Sheets

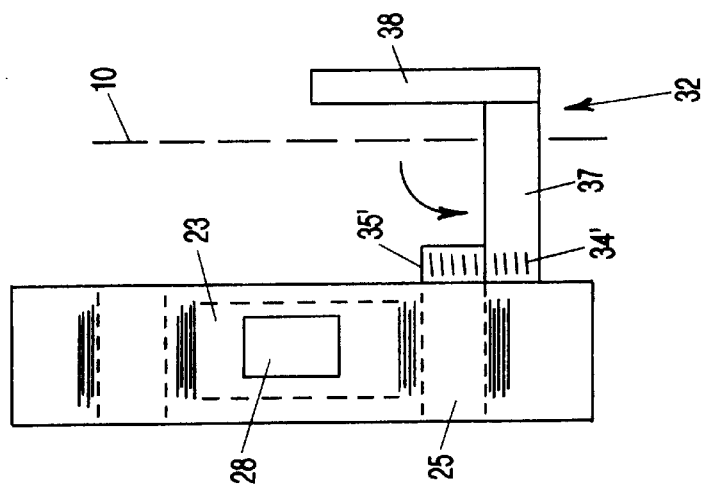
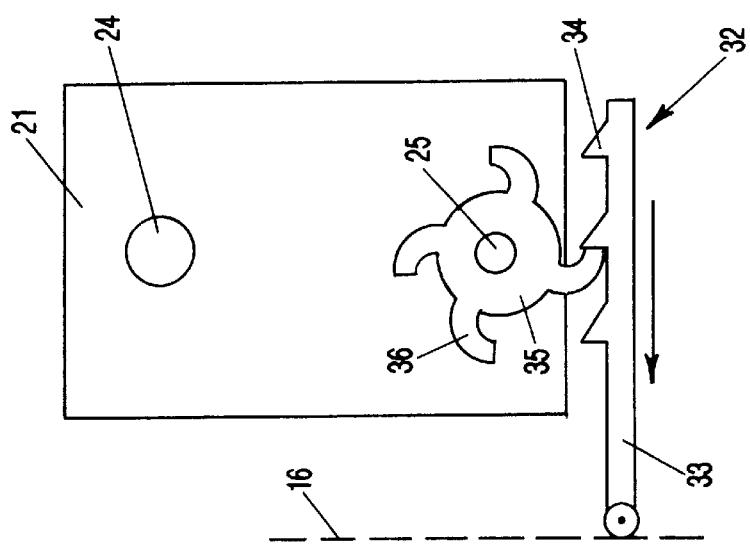
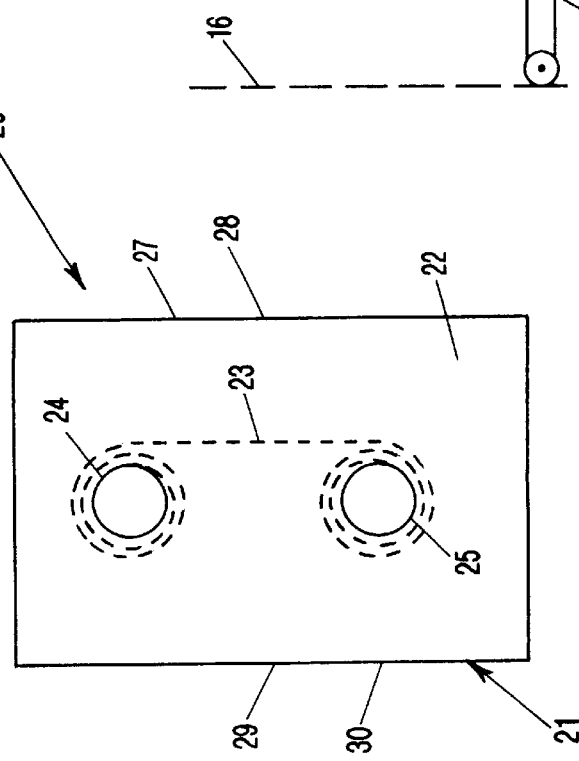

APPARATUS AND METHOD FOR PROTECTING COMPONENTS OF A LIGHT SOURCE

BACKGROUND OF THE INVENTION

The present invention relates to an apparatus and method for protecting at least one component, especially an optical component, of a light source.

Sources of light beams, and in particular laser systems, are used for ablating biological and non-biological substrates and for cutting various materials. In such applications, energy, especially laser energy, is applied to heat the substrate or material, or some component thereof, causing controlled vaporization. In the case of lasers, the systems thereof generally include a light source for generating laser light, and optical components for directing the laser beam to a target. The laser source may produce continuous or pulsed laser energy output. The delivery of laser energy to a target specimen and subsequent vaporization of a portion of the specimen often produces byproducts, such as smoke, carbonized particles and/or splattered particles from the specimen. These byproducts pose a threat to the consistent operation of the laser system in that they may be deposited upon the objective optics of the system, thus damaging or altering the optical components, reducing output power, distorting the pattern of energy distribution within the light or laser beam, or otherwise contributing to the degradation of the system.

One particular application of such laser systems includes laser finger perforators that are used to sample capillary blood for analysis of glucose and other blood chemistry measurement. The laser penetrates the finger by vaporizing and ablating tissue to create a small hole in the skin down to and including intersecting some of the capillaries. The vapor and additional small particles that are ablated when creating the hole in the finger can adhere to the surface of the laser lens. As described above, such adhered material will change the characteristics of the lens, such as its focus and light transmission parameters. These resultant changes can cause pain to the patient and/or make it more difficult to draw blood.

In view of the foregoing, it can be seen that there is a great need for providing means to protect the components of a light source, and in particular the optics thereof. This has been addressed by the prior art in several ways. One such way is to position the optics at a distance from a specimen that is great enough that vaporized or ablated material from the target area cannot reach the optics. Such a passive approach makes for a rather large device and is not a satisfactory solution. U.S. Pat. No. 5,148,446, Radich, discloses the protection of the objective lens of a laser system by directing a flowing fluid, such as air, over and away from the surface of the lens, thus directing ejected particulates away from such lens. This system is complicated and expensive, generally requires external power supply and pumps, and is not amenable to miniaturization. Also known are disposable protective devices that are manually inserted between the objective optics of laser system and the source of possible ablated material. Such protective devices are single-use components that must be discarded and replaced for each procedure (see PCT publications WO 98/04201 and WO 98/47435).

It is therefore an object of the present invention to provide an improved means for protecting components of a light source, and in particular an apparatus and method that can be used for extended procedures and/or for multiple procedures, thereby reducing the amount of waste generated, the number of disposable components that need to be provided, the danger of forgetting to replace a used protective device, and possibly also reducing the cost of operation of such a system.

BRIEF DESCRIPTION OF THE DRAWINGS

This object, and other objects and advantages of the present invention, will appear more clearly from the following specification in conjunction with the accompanying schematic drawings, in which:

FIG. 2a illustrates one exemplary embodiment of the inventive protection apparatus;

FIGS. 2b and 2c show exemplary advancement means for the protection apparatus of FIG. 2a;

SUMMARY OF THE INVENTION

Figure 1:
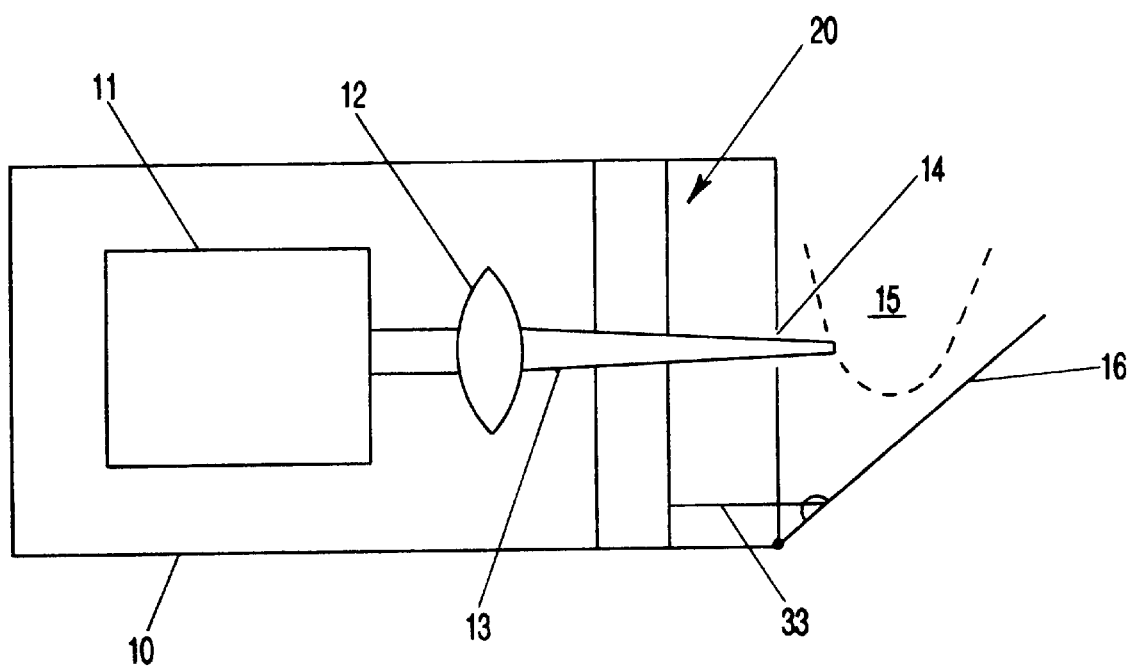
FIG. 1 illustrates a laser finger perforator employing the novel protection apparatus of the present invention.

The inventive apparatus and method for protecting at least one component of a light source are characterized primarily by means for shielding the component, and by means for advancing the shielding means. The means for shielding is held by the light source, and especially by a housing thereof, and is provided with a plurality of locations that are substantially transparent to an emission wave length of the light source, with such means for shielding being positioned such that during use of the light source, one of the substantially transparent locations is disposed between the component of the light source and an object that is to be irradiated. The means for advancing the shielding means operates upon activation of the light source or an element thereof, such as a control lever, lens cover, etc., in order to be able to dispose a different one of the substantially transparent locations of the shielding means between the component of the light source and the object that is to be irradiated.

The present invention thus discloses a device for use with light sources, and especially laser systems, with such device being replaceable or disposable after multiple use thereof. The inventive device or apparatus includes a substantially transparent location, such as a thin strip or sheet of film, glass or crystalline material, that is disposed between an object, such as the surface of skin, and an optical element of the light source. The area of the substantially transparent material either has a cross-sectional area that is many times that of the light beam that is emitted by the light source, or has several such sections. Thus, the area of the lens shielding means through which the light beam passes can be renewed, i.e., a fresh section can be provided, by moving a new section of material to the area through which the beam of light passes.

The inventive apparatus can be disposed of and replaced after the multiple substantially transparent locations of the shielding means thereof have been all used. Alternatively, the shielding means of the inventive apparatus can be in the form of an endless or reversible strip or disk, which can then be continuously or periodically cleaned to remove material that has adhered thereto, thus affording the inventive apparatus a very long useful life.

Further specific features of the present invention will be described in detail subsequently.

DESCRIPTION OF PREFERRED EMBODIMENTS

Referring now to the drawings in detail, although the present invention will be described primarily in conjunction with a laser device for perforating the skin of a living being, it is to be understood that any other device that uses a light source and involves potential splattering of a lens or other critical components of the device with debris, for example with blood, body fluid or non-living matter, and therefore requires protection of such component, is contemplated by the present invention.

FIG. 1 schematically illustrates a laser perforator that is provided with the novel protection apparatus of this invention, which is generally indicated by the reference numeral 20. The laser perforator includes a housing 10 in which is disposed a light source 11, which in the illustrated embodiment is a laser source. The laser perforator also includes a lens or other optical component 12 through which the laser source 11 emits a light beam 13, here a laser beam, which is then focused by the lens 12. The focused laser beam 13 exits the housing 10 via the aperture 14, whereupon the beam 13 perforates the skin surface 15. Hingedly connected to the housing 10 is an optional lens cover 16. The protection apparatus or lens shield 20 is disposed between the lens or optical component 12 and the aperture 14 in the housing 10. Although the lens shield 20 is shown as extending over the entire width of the housing 10, it need not do so.

One preferred specific embodiment of the inventive lens shield 20 is illustrated in FIGS. 2a and 2b. In particular, in this embodiment the lens shield 20 is in the form of a reel-to-reel or spool-to-reel cartridge or cassette 21. This cartridge has a housing 22 in which is disposed a thin strip of film 23 that is initially wound on a first spool 24 (or similar film storage means) and extends to a second spool or reel 25 that is adapted to receive the film 23 from the first spool. The film 23 is substantially transparent to an emission wavelength of the light source 11, in other words, is substantially transparent to the laser beam 13. Since the strip of film 23 has a given length, it has a plurality of substantially transparent locations for the laser beam 13, with such plurality of locations being provided by advancement of the film 23 in a manner to be described in detail subsequently. To allow the laser beam 13 to pass through the lens shield 20, one side 27 of the housing 22 of the cartridge 21 is provided with a window 28 in front of which the strip of film 23 passes. A window 29 is aligned with the window 28 on an opposite side 30 of the housing 22. Alternatively, the side 30 of the housing 22 could be essentially open. The cartridge 21 can be removably supported in the housing 10 of the laser perforator, for example in brackets provided on the housing.

The inventive protection apparatus or lens shield 20 is also provided with means 32 for advancement of the shield means, in other words, the strip of film 23. FIG. 2b shows one exemplary embodiment of such advancement means, which in this case is an automatic advancement means. In the illustrated embodiment, a rod 33 is pivotably mounted to the lens cover 16 of the laser perforator. The rod 33 is a rack that is provided with teeth 34 that mesh with a tined wheel 35 that is mounted on the winding spool 25. Thus, when the lens cover 16 is opened in order to be able to use the laser perforator, the rod 33 will be pulled in the direction of the arrow through a slot in the end wall of the housing 10 and will rotate the wheel 35 as a result of engagement of one of the teeth 34 with one of the tines 36, thereby rotating the spool 25 and hence automatically winding the strip of film 23 further onto the spool 25 and thereby advancing a clean location of the film 23 in front of the window 28 of the cartridge 21. When the film is completely used, the cartridge can be removed and disposed of; a new cartridge 21 is then inserted into the housing 10.

It is to be understood that other means for activating the advancement means 32 could also be provided. For example, as shown in FIG. 2c, a rod 37 could be connected to a control lever 38 or wheel on the housing 22. One end of the rotatably mounted rod 37 is provided with teeth 34' that are adapted to mesh with the teeth of a wheel 35', which is mounted on the spool 25 and can be a toothed gear or a tined wheel similar to the wheel 35 of the advancement means 32 illustrated in FIG. 2b. When the lever 38 is pulled, the rod 37 rotates in the direction of the arrow, thereby rotating the wheel 35' and hence the spool 25, thereby again advancing the film or strip 23. The teeth 34' of the rod 37 could also mesh with internal teeth provided in the spool 25 or an extension thereof. In addition, the rod 33 or 37 could be connected to a separate motor that could be activated by an on/off switch or that can be electronically controlled in response to operating parameters of the laser perforator. Such a motor could also be directly connected to the winding spool 25. Thus, the means for advancing the film or other shield means could be automatically or manually activated means, such as mechanical linkage means or electronic means.

The laser perforator, or similar light-emitting device, can be provided with an interlock or disabling means so that the device cannot be operated unless a shield means is present at all and/or the advancement means has operated to dispose a clean or renewed section of the strip of film or shield means in the path of the light beam 13 that is to be emitted. The light-emitting device can also be provided with a sensor or other means to detect and indicate whether or not a cartridge 21 or other type of lens shield has been inserted into the device.

In the embodiment illustrated in FIGS. 2a–2c the strip of film 23 is provided in the cartridge 21. However, it is to be understood that a strip of film similar to the film 23 could be wound directly onto spools that are preferably both rotatably mounted on the housing 10. In such a case, rather than replacing the cartridge 21, the strip of film 23 itself would have to be replaced.

Figure 3A:
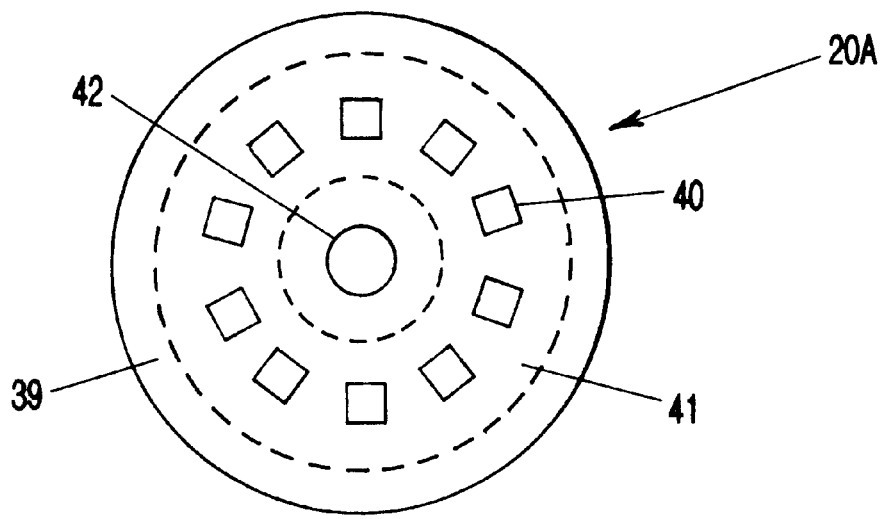
FIGS. 3a–3c show further exemplary embodiments of the inventive protection apparatus in the form of disks.

FIG. 3a shows a further exemplary embodiment of the inventive protection apparatus or lens shield, which in this case is indicated generally by the reference numeral 20A. In this embodiment, the lens shield is in the form of a disk 39 that is provided with a plurality of windows 40. A sheet 41 of film, glass or crystalline material, which as in the case of the strip or film 23 is substantially transparent to an emission wavelength of the light source, is disposed behind the windows 40. Rather than utilizing the sheet 41, it would also be possible to provide discrete pieces of film, glass or crystalline material behind each individual window 40. As was the case with the lens shield 20, the lens shield 20A is disposed between the optical component 12 and the aperture 14. The disk 39 is again advanced by advancement means, similar to the means 32 of the previously described embodiments, in order to advance the windows 40 in front of the aperture 14 of the housing 10. This can be accomplished, for example, by providing the rod 37 with teeth that can engage internal teeth provided in the central portion 42 of the disk 39, or by having the teeth 34 of the rack 33 engage teeth provided on the periphery of the disk 39.

Figure 3B:
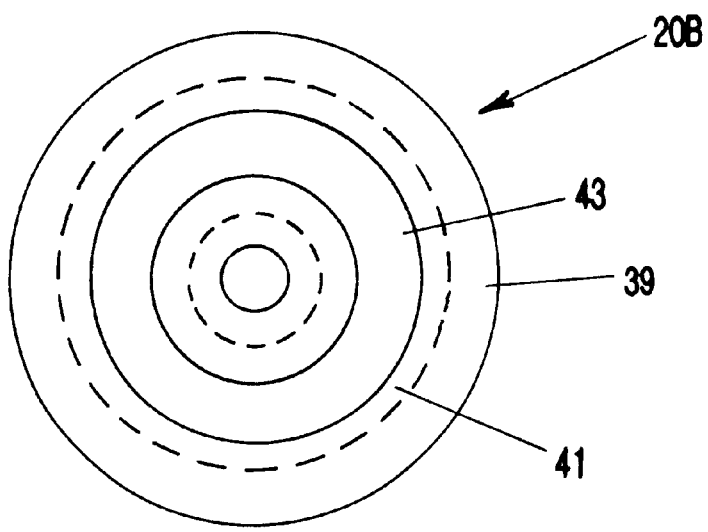

In the embodiment illustrated in FIG. 3b, rather than having discrete windows 40, the disk 39 is provided with a continuous window 43, thus exposing a ring of the sheet 41 of film, glass or crystalline material.

Figure 3C:
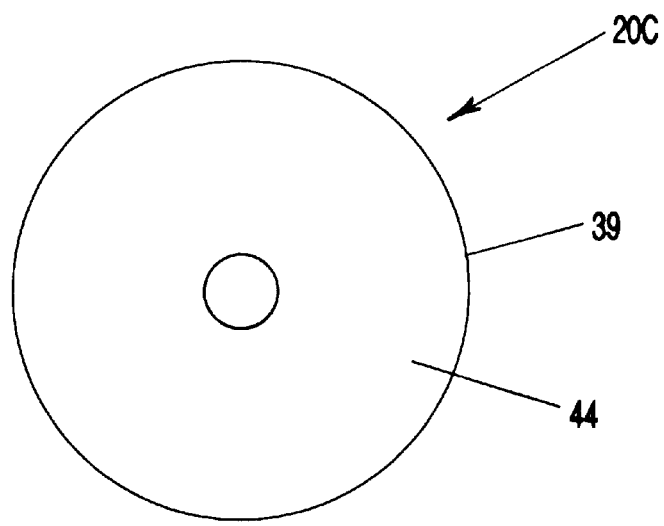

The lens shield 20C of the FIG. 3c is a disk 39 formed entirely of, for example, glass or crystalline material 44.

Figure 4:
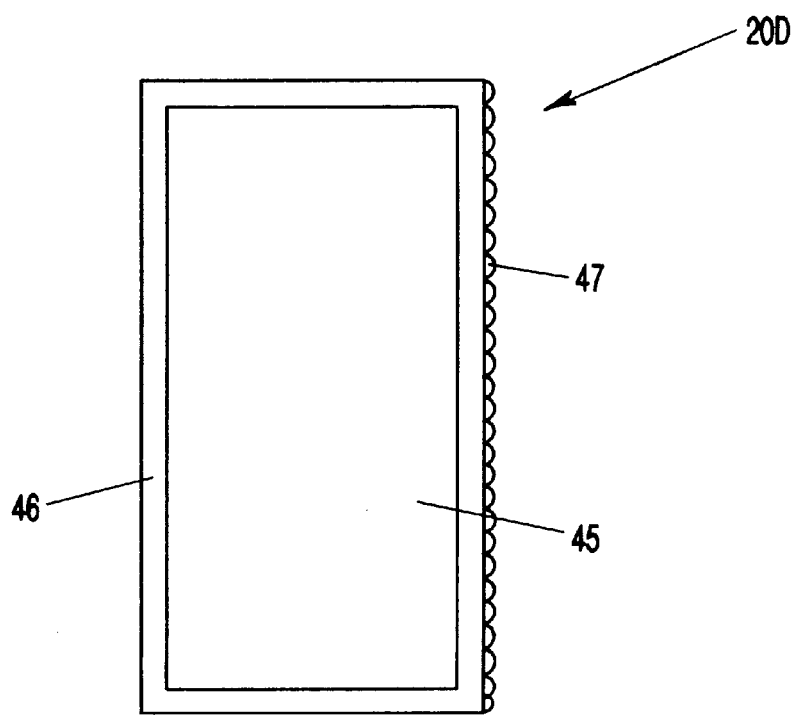
FIG. 4 shows another exemplary embodiment of an inventive protection apparatus.

A further exemplary lens shield 20D is illustrated in FIG. 4. In this embodiment, a thin sheet of film, glass or crystalline material 45 is disposed in a frame 46, which can be made of any suitable material, including plastic, cardboard or metal, as is also the case with the embodiments of FIG. 3a and 3b. The lens shield 20D could also be provided with discrete windows as in the previously described embodiment. To advance the lens shield 20D through the housing 10, the means 32 for advancement can, via an appropriate gear wheel or the like, engage the sprocket means 47 provided on one side of the frame 46.

It is to be understood that in all of the illustrated embodiments, the plane of the film, glass or crystalline material 23, 41, 44 or 45, when the same is aligned with the aperture 14 of the housing 10, is generally perpendicular to the axis of the light or laser beam 13.

It should be noted that the strip of film could also be an endless strip or a reversible strip. In such a case, a cleaning means is provided for cleaning the film. Such a cleaning means could also be provided for the disks of FIGS. 3a–3c, or the sheet of FIG. 4.

Instead of the housing 10 being provided with an end wall that is then provided with the aperture 14 for the light beam 13, the inventive protection apparatus or lens shield 20–20D could itself form the end of the housing 10.

It should also be noted that where the objective lens of the light source or laser device is required to be a focusing lens for certain applications in order to generate relatively high laser energy at a target surface, it is preferable in such instances to locate the inventive lens shield at a distance from the area of highest intensity in order to avoid thermal damage to the lens shield material, especially the strip or sheet of film, glass, or crystalline material.

As indicated previously, the rate of advance of the various lens shields of the present invention could be controlled as a function of various parameters of the light source device. For example, when used with a continuous wave type laser device, the lens shield could be advanced continuously at a rate dependent upon the output power of the laser device, moving slowly when a low power is used and more quickly when high power is being used, and stopping altogether when no laser light is being emitted. Similarly, when used with a pulsed laser device the lens shield could be advanced after each pulse, or after a given number of pulses. Furthermore, as indicated previously, the lens shield could be automatically advanced each time that the light or laser device is activated.

The glass, film or crystalline material of the inventive lens shields has a thickness preferably ranging from 20 $\mu$m to 2 mm. As indicated, the thin sheet or strip can be made of glass, polymeric material, such as polyester or polypropylene, or crystalline material, such as sapphire, CaCl, garnets, including yttrium aluminum garnet (YAG), and other suitable materials. The selection of material depends upon the requirements and properties of the laser system. The lens shield could be provided to produce simultaneous controlled alteration of the laser beam, for example, polarization, spatial filtering or spectral filtering of the beam as it passes through the strip or sheet of material. The glass, film or crystalline material could also be provided with a pattern such that the transparent areas differ in degree of transparency, diffractivity, or refractivity. Holographic filters could also be provided.

In view of the foregoing, it can be seen that this invention not only provides a new protection apparatus or lens shield for light-emitting sources, but also this invention provides a new method for protecting components of a light source.

The present invention is, of course, in no way restricted to the specific disclosure of the specification and drawings, but also encompasses any modifications within the scope of the appended claims.

What is claimed is:

1. An apparatus for protecting at least one component of a light source, comprising:

means for shielding said at least one component, wherein said means for shielding is held by said light source and has a plurality of locations that are substantially transparent to an emission wavelength of said light source, and wherein said means for shielding is positioned such that during the use of said light source, one of said substantially transparent locations of said means for shielding is disposed between said at least one component of said light source and an object that is to be irradiated, wherein said means for shielding comprises a thin strip or sheet of film, glass or crystalline material having an area that is greater than a cross-sectional area of a light beam emitted by said light source to thereby provide said plurality of substantially transparent locations of said means for shielding; and means for advancement of said means for shielding upon activation of said light source or an element thereof in order to be able to dispose a different one of said substantially transparent locations of said means for shielding between said at least one component of said light source and an object that is to be irradiated, wherein said film, glass or crystalline material is movably disposed in a cartridge that is removably disposed in a housing for said light source, and wherein said means for advancement of said means for shielding acts upon a take-up reel of said cartridge to advance said film, glass or crystalline material.

2. An apparatus for protecting at least one component of a light source, comprising:

means for shielding said at least one component, wherein said means for shielding is held by said light source and has a plurality of locations that are substantially transparent to an emission wavelength of said light source, and wherein said means for shielding is positioned such that during the use of said light source, one of said substantially transparent locations of said means for shielding is disposed between said at least one component of said light source and an object that is to be irradiated; and means for advancement of said means for shielding upon activation of said light source or an element thereof in order to be able to dispose a different one of said substantially transparent locations of said means for shielding between said at least one component of said light source and an object that is to be irradiated, wherein said means for advancement of said means for shielding comprises linkage means operatively connected to a housing for said light source and to said means for shielding for advancing same.

3. An apparatus according to claim 2, wherein said means for shielding comprises a thin strip or sheet of film, glass or crystalline material having an area that is greater than a cross-sectional area of a light beam emitted by said light source to thereby provide said plurality of substantially transparent locations of said means for shielding.

4. An apparatus according to claim 3, wherein said film is movably disposed in a cartridge that is removably disposed in a housing for said light source, and wherein said means for advancement of said means for shielding acts upon a take-up reel of said cartridge to advance said film.

5. An apparatus according to claim 2, wherein said film, glass or crystalline material is in the form of an endless or reversible strip, or disk.

6. An apparatus according to claim 2, wherein said linkage means is connected to a cover for a lens of said light source, to a power switch for said light source, or to a control means provided on said housing.

7. An apparatus according to claim 2, wherein an interlock device is provided for enabling said light source only when said means for advancement has advanced said means for shielding.

8. An apparatus according to claim 5, which includes means for cleaning said strip or disk.

9. An apparatus for protecting at least one component of a light source, comprising:

means for shielding said at least one component, wherein said means for shielding is held by said light source and has a plurality of locations that are substantially transparent to an emission wavelength of said light source, and wherein said means for shielding is positioned such that during the use of said light source, one of said substantially transparent locations of said means for shielding is disposed between said at least one component of said light source and an object that is to be irradiated, wherein said means for shielding comprises a thin strip or sheet of film, glass or crystalline material having an area that is greater than a cross-sectional area of a light beam emitted by said light source to thereby provide said plurality of substantially transparent locations of said means for shielding; and means for advancement of said means for shielding upon activation of said light source or an element thereof in order to be able to dispose a different one of said substantially transparent locations of said means for shielding between said at least one component of said light source and an object that is to be irradiated, wherein said film, glass or crystalline material is disposed in a flat frame that is removably disposed in a housing for said light source, and wherein said means for advancement of said means for shielding acts upon said frame to advance same and hence said film, glass or crystalline material.

10. An apparatus for protecting at least one component of a light source, comprising:

means for shielding said at least one component, wherein said means for shielding is held by said light source and has a plurality of locations that are substantially transparent to an emission wavelength of said light source, and wherein said means for shielding is positioned such that during the use of said light source, one of said substantially transparent locations of said means for shielding is disposed between said at least one component of said light source and an object that is to be irradiated; and means for advancement of said means for shielding upon activation of said light source or an element thereof in order to be able to dispose a different one of said substantially transparent locations of said means for shielding between said at least one component of said light source and an object that is to be irradiated, wherein said means for shielding comprises a disk having discrete windows, in each of which is disposed a thin sheet or strip of film, glass or crystalline material, wherein said disk is removably disposed in a housing for said light source, and wherein said means for advancement of said means for shielding acts upon said disk to advance said windows thereof.

11. A method of protecting at least one component of a light source, including the steps of:

providing means for shielding having a plurality of locations that are substantially transparent to an emission wavelength of said light source, wherein said step of providing means for shielding comprises providing a thin strip or sheet of film, glass or crystalline material having an area that is greater than a cross-sectional area of a light beam emitted by said light source to thereby provide said plurality of substantially transparent locations of said means for shielding;

movably disposing said film in a cartridge;

removably disposing said cartridge in a housing for said light source such that during use of said light source, one of said substantially transparent locations of said means for shielding is adapted to be disposed between said at least one component of said light source and an object that is to be irradiated; and advancing said means for shielding, upon activation of said light source or an element thereof, for disposing a different one of said substantially transparent locations of said means for shielding between said at least one component of said light source and an object that is to be irradiated, wherein said step of advancing said means for shielding comprises the step of acting upon a take-up reel of said cartridge to advance said film.

12. A method according to claim 11, wherein said step of advancing said means for shielding comprises the step of advancing said means for shielding as a function of emission of energy from said light source.

13. A method according to claim 11, wherein said step of advancing said means for shielding comprises the step of advancing said means for shielding as a function of a given number of emission pulses or a given period of time.

14. A method according to claim 11, wherein said step of advancing said means for shielding comprises the step of continuously or intermittently advancing said means for shielding during operation of said light source.

15. A method of protecting at least one component of a light source, including the steps of:

providing means for shielding having a plurality of locations that are substantially transparent to an emission wavelength of said light source, wherein said step of providing means for shielding comprises providing a thin strip or sheet of film, glass or crystalline material having an area that is greater than a cross-sectional area of a light beam emitted by said light source to thereby provide said plurality of substantially transparent locations of said means for shielding;

disposing said film, glass or crystalline material in a flat frame;

removably disposing said frame in a housing for said light source such that during use of said light source, one of said substantially transparent locations of said means for shielding is adapted to be disposed between said at least one component of said light source and an object that is to be irradiated; and advancing said means for shielding, upon activation of said light source or an element thereof, for disposing a different one of said substantially transparent locations of said means for shielding between said at least one component of said light source and an object that is to be irradiated, wherein said step of advancing said means for shielding comprises the step of acting upon said frame to advance same and hence said film, glass or crystalline material.

16. A method of protecting at least one component of a light source, including the steps of:

providing a thin sheet or strip of film, glass or crystalline material in the form of a disk for shielding having a plurality of locations that are substantially transparent to an emission wavelength of said light source;

removably disposing said disk in a housing for said light source such that during use of said light source, one of said substantially transparent locations of said means for shielding is adapted to be disposed between said at least one component of said light source and an object that is to be irradiated; and advancing said means for shielding, upon activation of said light source or an element thereof, for disposing a different one of said substantially transparent locations of said means for shielding between said at least one component of said light source and an object that is to be irradiated, wherein said step of advancing said means for shielding comprises the step of acting upon said disk to advance same.

17. A method according claim 16, which includes the step of disposing said thin sheet or strip of film, glass or crystalline material in a discrete or continuous window of said disk, wherein said step of advancing said means for shielding comprises the step of acting upon said disk to advance said window or windows thereof.

* * * * *